(12) United States Patent
LeMay et al.

(10) Patent No.: US 8,372,027 B2
(45) Date of Patent: Feb. 12, 2013

(54) TAMPON APPLICATOR ASSEMBLY

(75) Inventors: Jessica Elizabeth LeMay, New York, NY (US); Keith Edgett, Middletown, DE (US); George S. Jarmon, Camden/Wyoming, DE (US); Kathryn Bennett, Fairfield, CT (US)

(73) Assignee: Playtex Products, Inc., Westport, CT (US)

( * ) Notice: Subject to any disclaimer, the term of this patent is extended or adjusted under 35 U.S.C. 154(b) by 285 days.

(21) Appl. No.: 10/619,892

(22) Filed: Jul. 15, 2003

(65) Prior Publication Data

US 2004/0199102 A1 Oct. 7, 2004

Related U.S. Application Data

(63) Continuation-in-part of application No. 10/407,855, filed on Apr. 4, 2003, now abandoned.

(51) Int. Cl.
*A61F 13/20* (2006.01)
(52) U.S. Cl. .............................. 604/15; 604/14
(58) Field of Classification Search .............. 604/11–18, 604/385.19, 904
See application file for complete search history.

(56) References Cited

U.S. PATENT DOCUMENTS

| | | |
|---|---|---|
| 652,848 A | 7/1900 | Hill |
| 1,171,736 A | 2/1916 | McClanahan ................... 292/37 |
| 2,476,956 A | 6/1940 | Bonham |
| 2,489,502 A | 7/1946 | Ruth |
| 2,587,717 A | 8/1947 | Fourness |
| D197,751 S | 3/1964 | Rigney et al. |
| 3,139,886 A | 7/1964 | Tallman et al. |
| 3,575,169 A | 4/1971 | Voss et al. ..................... 128/263 |
| 3,628,533 A | 12/1971 | Loyer ............................ 128/263 |
| 3,765,416 A | 10/1973 | Werner et al. ................... 604/18 |
| 4,048,998 A | 9/1977 | Nigro ............................ 128/263 |
| D250,663 S | 12/1978 | Koch et al. ...................... D24/99 |
| 4,198,978 A | 4/1980 | Nigro ............................. 604/14 |
| 4,361,150 A * | 11/1982 | Voss ............................... 604/15 |
| 4,421,504 A | 12/1983 | Kline ............................. 604/12 |
| 4,428,370 A | 1/1984 | Keely ............................ 128/838 |
| 4,508,531 A | 4/1985 | Whitehead ...................... 604/14 |
| 4,536,178 A | 8/1985 | Lichstein et al. ............... 604/15 |
| 4,676,773 A | 6/1987 | Sheldon .......................... 604/16 |
| 4,846,802 A * | 7/1989 | Sanders, III ..................... 604/15 |

(Continued)

FOREIGN PATENT DOCUMENTS

| | | |
|---|---|---|
| EP | 0418791 A1 | 3/1991 |
| JP | 04322647 A | 11/1992 |

(Continued)

OTHER PUBLICATIONS

Office Action from related U.S. Appl. No. 10/619,677 dated Oct. 9, 2007.

(Continued)

*Primary Examiner* — Lynne Anderson
(74) *Attorney, Agent, or Firm* — Ohlandt, Greeley, Ruggiero & Perle, L.L.P.

(57) ABSTRACT

A tampon applicator assembly having a barrel, a plunger, and a pledget is provided. The barrel has an insertion tip, a main section, and a finger grip. The main section can have a maximum outer dimension located closer to the finger grip than to the insertion tip and/or can have a main section taper ratio of about 1.07 to about 1.15. The insertion tip can have a taper ratio of more than about 0.66 and/or a plurality of petals with a petal length-to-width ratio over about 2 to less than about 3.

17 Claims, 3 Drawing Sheets

U.S. PATENT DOCUMENTS

| | | | | |
|---|---|---|---|---|
| 4,891,042 | A | | 1/1990 | Melvin et al. .................. 604/18 |
| 4,921,474 | A | | 5/1990 | Suzuki et al. ................... 604/16 |
| 5,080,659 | A | | 1/1992 | Nakanishi ....................... 604/15 |
| 5,158,535 | A | * | 10/1992 | Paul et al. ....................... 604/15 |
| 5,290,501 | A | | 3/1994 | Klesius .......................... 264/322 |
| 5,453,085 | A | * | 9/1995 | Schoelling ..................... 604/15 |
| 5,531,674 | A | * | 7/1996 | Frayman ........................ 604/11 |
| 5,788,663 | A | | 8/1998 | Igaue et al. ..................... 604/15 |
| D415,565 | S | | 10/1999 | Hayes et al. ................. D24/141 |
| 6,045,526 | A | | 4/2000 | Jackson .......................... 604/15 |
| 6,264,626 | B1 | * | 7/2001 | Linares et al. .................. 604/15 |
| 6,364,854 | B1 | | 4/2002 | Ferrer et al. .................... 604/60 |
| 6,368,442 | B1 | * | 4/2002 | Linares et al. ................ 156/198 |
| 6,423,025 | B1 | * | 7/2002 | Buzot .............................. 604/15 |
| 6,432,075 | B1 | | 8/2002 | Wada et al. ..................... 604/15 |
| 6,432,076 | B1 | * | 8/2002 | Wada et al. ..................... 604/15 |
| 6,478,764 | B1 | * | 11/2002 | Suga ............................... 604/15 |
| 7,172,573 | B1 | | 2/2007 | Lamb .............................. 604/59 |
| 2004/0199102 | A1 | | 10/2004 | LeMay et al. .................. 604/11 |

FOREIGN PATENT DOCUMENTS

| | | |
|---|---|---|
| JP | 04322648 A | 11/1992 |
| JP | 2000-279446 | 10/2000 |
| JP | 2001-145658 | 5/2001 |
| JP | 62-094156 | 4/2007 |

OTHER PUBLICATIONS

U.S. Appl. No. 10/242,474, filed Sep. 12, 2002, LeMay et al.
Second Examiner's Report from Australian Patent Application No. 2004228004 dated Jan. 4, 2010.
Notice on Reasons for Rejection from Japanese Patent Application No. 2006-509630 dated Dec. 2, 2009.
Decision of Rejection (with Decision of Rejection of Amendment) from corresponding Japanese Application No. 2006-509630 mailed Aug. 17, 2010.
Japanese Office Action dated Jun. 26, 2012 from JP Appln No. 2010-281744.

* cited by examiner

TAMPON APPLICATOR ASSEMBLY

CROSS-REFERENCE TO RELATED APPLICATIONS

This application is a continuation-in-part of U.S. application Ser. No. 10/407,855 filed on Apr. 4, 2003 now abandoned, the contents of which are incorporated by reference.

BACKGROUND OF THE INVENTION

1. Field of the Invention

The present invention is related to a tampon applicator assembly. More particularly, the present invention is related to an improved tampon applicator assembly that increases the ease of use and user comfort.

2. Description of Related Art

A tampon applicator assembly is used to inject an absorbent or hygienic material, known as a tampon pledget, into a vaginal cavity. Commercial tampon applicator assemblies typically have a barrel and a plunger used to expel a pledget housed in the barrel.

The use of such assemblies requires a user to grip the barrel and guide it easily into the vaginal cavity. This is particularly important since a portion or all of the assembly is out of a direct line of sight of the user during insertion. Accordingly, an assembly that is difficult to grip and control can hinder proper and comfortable delivery of the pledget.

Another problem associated with a difficult to grip and control assembly is that the user often applies excessive gripping force on the barrel to compensate for the lack of gripability. This excessive force may partially deform and damage the barrel and/or plunger, thereby distorting the assembly and obstructing the normal pathway of the pledget therefrom. As a result, the user may be required to apply a significant amount of force to eject the pledget from the assembly, which may result in discomfort to the user.

Many factors combine to increase the comfort of the user during the use of tampon applicator assemblies. For example, the user's comfort can be affected by one or more ease factors. These ease actors can include the ease with which: the assembly is inserted into the vagina, the pledget is expelled from the assembly, and the spent assembly is removed from the vagina. Thus, there is a need to provide improved tampon applicator assemblies, which increase the user's comfort by addressing one or more of the aforementioned ease factors.

BRIEF SUMMARY OF THE INVENTION

It is an object of the present invention to provide an easy to use tampon applicator assembly, which is easy to grip and control during insertion and removal of the applicator assembly, as well as during expulsion of the pledget.

It is another object to provide a tampon applicator assembly having petals with a length-to-width ratio that facilitates expulsion of the pledget.

It is yet another object to provide a tampon applicator assembly having a plunger with one or more tapered ends to facilitate expulsion of the pledget.

It is a further object of the present invention to provide a tampon applicator assembly having a barrel with tapered tip and a tapered main section, which facilitates insertion and removal of the applicator assembly.

It is still a further object of the present invention to provide a tampon applicator assembly having a barrel with a finger grip having a shoulder and a flare, which facilitates insertion and removal of the applicator assembly.

These and other objects of the present invention are provided by a tampon applicator assembly having a barrel, a plunger, and a pledget. The barrel has an insertion tip, a main section, and a finger grip. The main section has a maximum outer dimension located closer to the finger grip than to the insertion tip.

The present invention also provides a tampon applicator assembly having a barrel, a plunger, and a pledget. The barrel has an insertion tip, a main section, and a finger grip, in which the main section has a taper ratio of about 1.07 to about 1.15.

The present invention also provides a tampon applicator assembly in which the finger grip has a gripping region disposed between a shoulder region and a flared region. The shoulder and flared regions are about 10% to about 30% larger than the gripping region.

A tampon applicator assembly is also provided in which the insertion tip has a plurality of petals and an insertion tip having a taper ratio of more than about 0.66.

In addition, the present invention provides a tampon applicator assembly in which the insertion tip has a plurality of petals with a petal length-to-width ratio of over about 2 to less than about 3.

The above-described and other features and advantages of the present invention will be appreciated and understood by those skilled in the art from the following detailed description, drawings, and appended claims

DETAILED DESCRIPTION OF THE INVENTION

Figure 1:
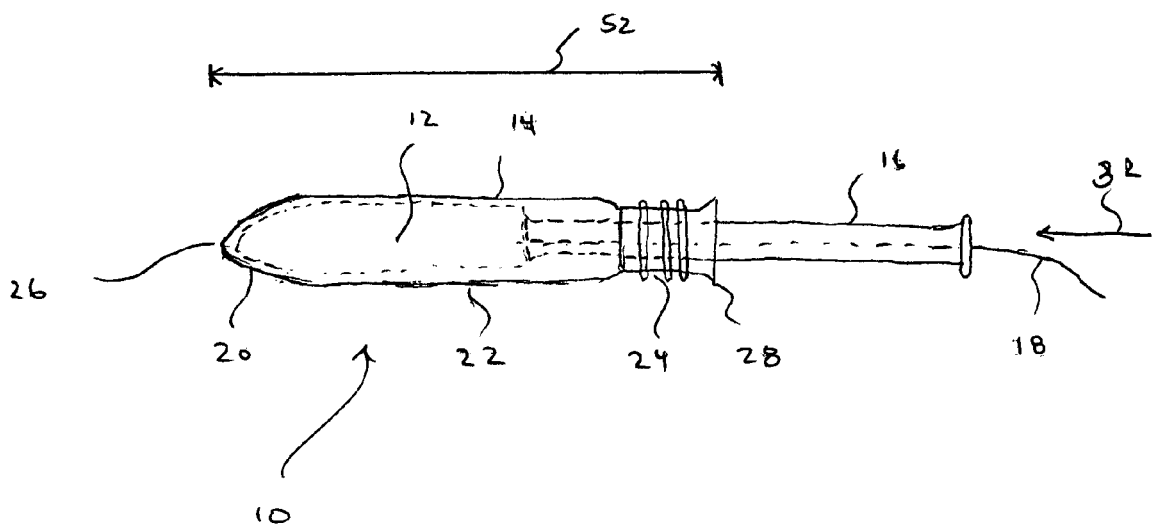
FIG. 1 is a side view of an exemplary embodiment of a tampon applicator assembly according to the present invention.
Figure 2:
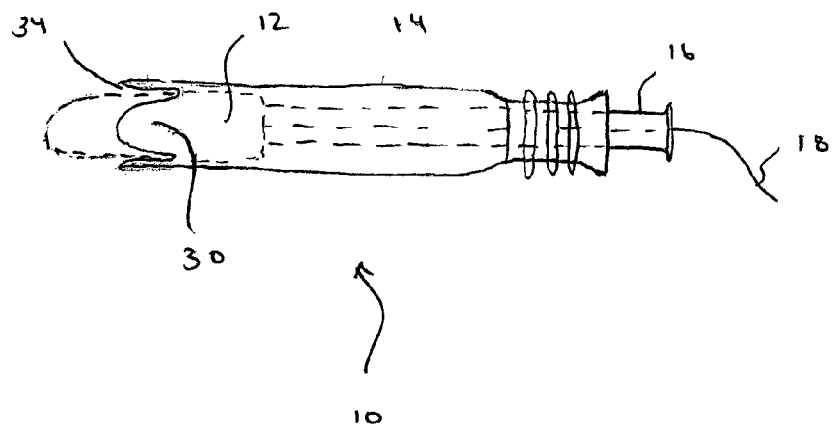
FIG. 2 is a side view of the assembly of FIG. 1 during expulsion of the pledget.

Referring now to the figures and more particularly to FIGS. 1 and 2, an exemplary embodiment of an improved tampon applicator assembly generally represented by reference numeral 10 is illustrated. The improved assembly 10 is easier to insert, use, and remove than prior tampon applicator assemblies.

Assembly 10 has a pledget 12, a barrel 14, and a plunger 16. Pledget 12 is disposed in barrel 14. Pledget 12 has a withdrawal cord 18 connected thereto, which extends through barrel 14 and plunger 16, and out of assembly 10.

Barrel 14 is sub-divided into three sections, namely an insertion tip 20, a main section 22, and a finger grip 24. Insertion tip 20 defines a first end 26 of barrel 14, while finger grip 24 terminates at a second end 28 of the barrel.

Plunger 16 can expel pledget 12 from barrel 14. For example, first end 26 can have a number or a plurality of petals 30 disposed about the end. Petals 30 open as shown in FIG. 2 upon application of a predetermined expulsion force by pledget 12. For example, petals 30 can open with an expulsion force of between about 8 ounces and about 40 ounces.

Plunger 16 is slidably disposed in barrel 14 at second end 28. Pledget 12 is expelled through first end 26 through the movement of plunger 16 in the direction of arrow 32. As plunger 16 moves in the direction of arrow 32, the plunger can urge pledget 12 into petals 30 until the petals open and the pledget is expelled from barrel 14 through first end 26.

Petals 30 are defined in insertion tip 20 by a number or plurality of slits 34. It should be recognized that insertion tip 20 of barrel 14 is illustrated by way of example as including four petals 30. Of course, insertion tip 20 having more or less than four petals 30 is contemplated by the present invention. For example, insertion tip 20 can have between about 2 to about 6 petals, preferably between about 3 to about 5 petals, more preferably about 4 petals.

Figure 3:
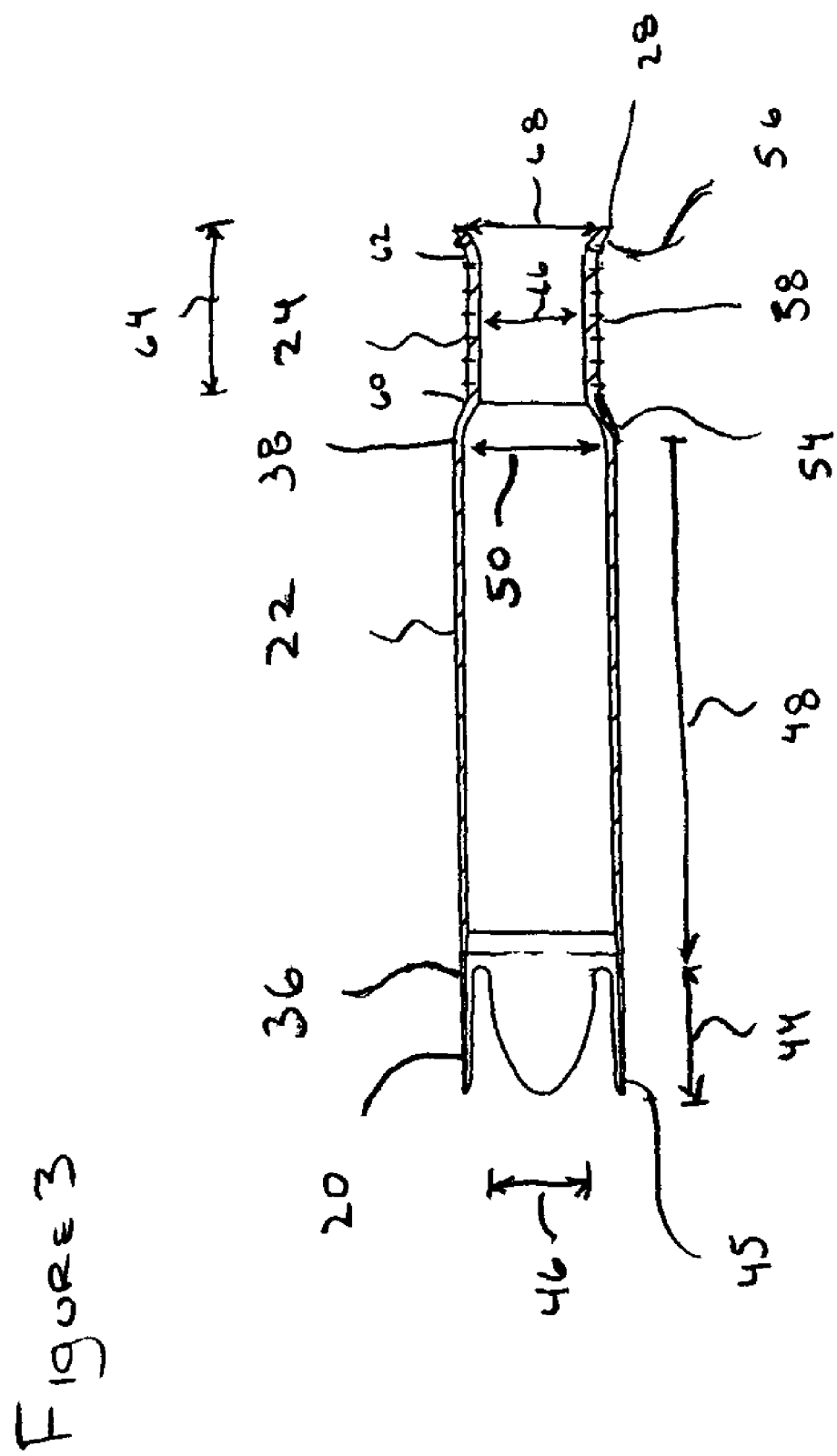
FIG. 3 is a sectional view of the barrel of FIG. 2.
Figure 4:
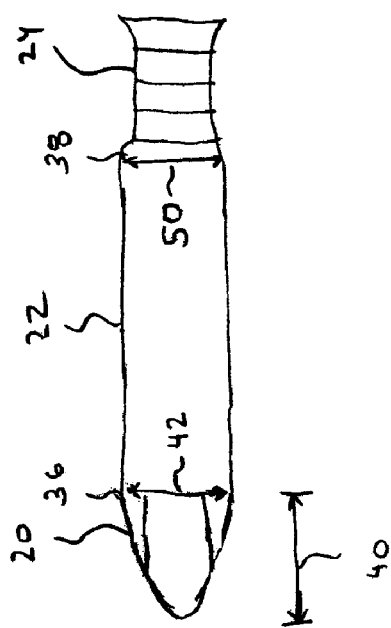
FIG. 4 is a side view of the barrel of FIG. 1.

Referring now to FIGS. 3 and 4, insertion tip 20 and main section 22 intersect at a first plane 36, while the main section and finger grip 24 intersect at a second plane 38.

When in a closed position (FIG. 1), petals 30 collectively provide insertion tip 20 with a shape that facilitates insertion. Through both qualitative and quantitative consumer research, it has been determined that providing insertion tip 20 with a taper greatly enhances the actual and perceived level of comfort associated with inserting barrel 14 of assembly 10.

Insertion tip 20 has a length 40 and an outer dimension 42. Length 40 is defined as the distance between first plane 36 and first end 26. Outer dimension 42 is tapered (e.g., decreases along length 40), linearly or non-linearly, from a maximum at first plane 36 to a minimum at first end 26. The taper of insertion tip 20 is defined as a ratio of length 40 of insertion tip 20 divided by the maximum outer dimension of the tip. The maximum outer dimension of insertion tip 20 is outer dimension 42 at first plane 36. Preferably, insertion tip 20 has a taper ratio of between about 0.55 and about 1.6, more preferably more than about 0.66. For example, in a preferred embodiment insertion tip 20 has a taper ratio of between about 0.66 and about 1.6, more preferably between about 0.7 and about 0.9.

Each petal 30 has a length 44 and a width 46. Preferably, insertion tip 20 has a petal length-to-width ratio is about 0.8 to about 3, more preferably over about 2 to less than about 3. As used herein, the petal length-to-width ratio is defined as length 44 divided by width 46. In a first exemplary embodiment, insertion tip 20 has three petals 30 and a petal length-to-width ratio of about 0.95. In an alternate exemplary embodiment, insertion tip 20 has six petals 30 and a petal length-to-width ratio of about 2.05.

Each petal 30 also has a thickness 45. Thickness 45 can be constant across length 44 of the petals. Alternately, thickness 45 can vary along length 44 of the petals. Generally, thickness 45 is proportional to the petal length-to-width ratio. For example, thickness 45 is larger for petals 30 having a large petal length-to-width ratio.

Further, it has been determined that providing main section 22 with a taper can also enhance the actual and perceived level of comfort associated with inserting barrel 14 of assembly 10.

Main section 22 has a length 48 and an outer dimension 50, which defines the maximum outer dimension of barrel 14. Length 48 is defined as the distance between first and second planes 36, 38. Outer dimension 50 is tapered (e.g., decreases along length 48), linearly or non-linearly, from a maximum outer dimension 50 at second plane 38 to a minimum outer dimension 42 at first plane 36.

The taper of main section 22 is defined as a ratio of dimension 50 at second plane 38 divided by dimension 42 at first plane 36. Preferably, main section 22 has a taper ratio of about 1.07 to about 1.15, and more preferably about 1.08 to about 1.13.

Barrel 14 has an overall length 52, which is defined as the distance between first and second ends 26, 28 as illustrated in FIG. 1. Second plane 38 is preferably located closer to second end 28 than to first end 26. Namely, second plane 38 and, thus, the maximum outer dimension of main section 22 (e.g., dimension 50) is located on barrel 14 more than half of overall length 52 from first end 26. Preferably, second plane 38 is located about 55% to about 85% of overall length 52 from first end 26, more preferably about 60% to about 75%.

This tapering of main section 22 facilitates insertion comfort by gradually parting the vulva-vaginal channel over a longer length of barrel 14 than that of only insertion tip 20.

It has also been determined that providing assembly 10 with finger grip 24 can enhance the actual and perceived level of comfort associated with inserting barrel 14 of assembly 10, expelling pledget 12 from the barrel, and removing the barrel.

Finger grip 24 is bounded by a shoulder region 54 and a flared region 56, which define a gripping region 58 therebetween. Shoulder region 54 intersects main section 22 at second plane 38 and intersects gripping region 58 at a third plane 60. Similarly, flared region 56 intersects gripping region 58 at a fourth plane 62 and terminates at second end 28.

Shoulder region 54 provides a firm grip surface during insertion of barrel 14 into the vaginal vault. Flared region 56 provides a firm grip surface during expulsion of pledget 12 from barrel 14, as well as during removal of the barrel from the body. Thus, regions 54, 56 can mitigate slipping of the user's fingers from gripping region 58.

Gripping region 58 may be concave, convex, flat, or any combinations thereof and has a length 64. Length 64 is defined as the distance between third and forth planes 60, 62. Length 64 is about 13 mm (0.5 inches) to about 25 mm (1 inch), more preferably about 17 mm (0.67 inches) to about 21 mm (0.83 inches), with about 19 mm (0.75 inches) being the most preferred.

Gripping region 58 has an outer dimension 66, which is substantially smaller than the outer dimension of regions 54, 56 at least at one plane along length 64. Gripping region 58 may be uniform in cross-sectional shape or area along length 64. By way of example, outer dimension 66 can be about 4.5 millimeters (mm) (0.175 inches) to about 20.5 mm (0.80 inches), more preferably about 11.5 mm (0.45 inches).

In the illustrated embodiment, shoulder region 54 has a maximum outer dimension 50 at second plane 38, while flared region 56 has a maximum outer dimension 68 at second end 28. Outer dimension 50 of shoulder region 54 may be the same as or different from outer dimension 68 of flared region 56.

Preferably, outer dimensions 50 or 68 are each larger than outer dimension 66. Outer dimension 50 is preferably about 10% to about 30% larger than outer dimension 66, more preferably about 25% larger. Further, outer dimension 68 is preferably about 10% to about 30% larger than outer dimension 66, more preferably about 15% larger.

Gripping region 58 may also include one or more gripping structures 70 to improve gripability of barrel 14. Suitable gripping structures 70 include, for example, one or more and preferably two or more, embossments, protuberances, slits, grooves, louvers, perforations, lances, abrasive medium, high wet coefficient of friction materials, pressure sensitive adhesives, or any combinations thereof. In addition, gripping structures 70 may be formed in any shape, including, for example, arc, circle, concave, cone, convex, diamond, line, oval, polygon, rectangle, rib, square, triangle, or any combinations thereof.

Figure 5:
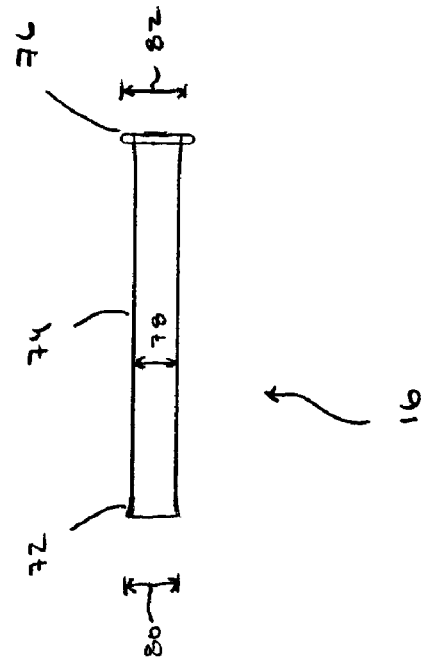
FIG. 5 is a side view of the plunger of FIGS. 1 and 2.

Plunger 16 is described with reference to FIG. 5. Plunger 16 has a first end 72, a main body 74, and a second end 76. In use, a user applies a force on second end 76 to move plunger 16 in barrel 14 as described above so that first end 72 acts on pledget 12.

Main body 74 has a cross-sectional shape, which is received within barrel 14 at second end 28. Preferably, main body 74 has an outer dimension 78 of at least about 4 mm (0.157 inches), with about 8.0 mm (0.315 inches) being preferred. In addition, it is preferred that outer dimension 78 of main body 74 be constant along the length of the main body to facilitate the transmission force from second end 76 to first end 72.

First end 72 facilitates distribution of force from plunger 16 to pledget 12. Additionally, first end 72 prevents plunger 16 from separating from barrel 16 through second end 28. Accordingly, first end 72 has an outer dimension 80, which is larger than outer dimension 78 of main body 72 and larger than outer dimension 68 of second end 28.

Second end 76 has an outer dimension 82, which is sized to receive the finger of a user. Accordingly, outer dimension 82 is preferably larger than outer dimension 78 of main body 74. For example, outer dimension 82 can be about 10% to about 25% larger than outer dimension 78 of main body 72, more preferably outer dimension 82 is about 15% larger than outer dimension 78. For example, outer dimension 82 of second end 76 can be about 10.4 mm (0.41 inches) and outer dimension 78 of main body 72 can be about 9 mm (0.35 inches).

Second end 76 can have a gradual enlargement or taper from outer dimension 78 to outer dimension 82, such as a trumpet shape. Alternately, second end 76 can have an abrupt enlargement from outer dimension 78 to outer dimension 82, such as an abrupt ledge. Plunger 16 can be formed by any suitable method, such as, molding and extrusion. In addition, outer dimensions 80 and 82 can be provided on plunger 16 by methods, such as, but not limited to, molding, post-forming, rolling, or attaching an additional piece to the plunger.

It is contemplated by the present invention that outer dimension 68 of barrel 14 be the same as, smaller than, or larger than outer dimension 82 of plunger 16. Preferably, outer dimension 68 of barrel 14 is the same as outer dimension 82 of plunger 16.

Assembly 10 provides a combination of features, which achieve consumer benefits unavailable in prior assemblies. For example, assembly 10 is easily and comfortably inserted into the body. Here, the tapers of insertion tip 20 and main section 22 combine to gradually part the vulva-vaginal channel, while shoulder region 54 of finger grip 24 provides the user with a firm grip on barrel 14.

Additionally, assembly 10 increases the comfort of the user by providing an assembly from which pledget 12 can be easily expelled. The combination of the petal ratio, the length-to-width ratio of petals 30, and the outer dimensions of first and second ends 72, 74 of plunger 16 all combine to increase the ease and comfort of expelling pledget 12 from barrel 14. Further, flared region 56 of finger grip 24 provides the user with a firm grip on barrel 14 during the expulsion of the pledget 12 from the barrel.

Further, assembly 10 is easily and comfortably removed from the body. Again, the tapers of insertion tip 20 and main section 22, as well as flared region 56 of finger grip 24 combine to increase the ease, comfort, and grip during the removal of assembly 10.

Suitable materials for forming barrel 14 and/or plunger 16 include, for example, biopolymer, cardboard, heat shrink plastic, paper slurry, plastic, plastic tubing, pulp slurry, pulp-molded paper, or any combinations thereof. By way of example, barrel 14 can be formed of low-density polyethylene (LDPE) and plunger 16 can be formed of axially oriented high-density polyethylene (HDPE). In addition, barrel 14 and/or plunger 16 may be coated with a coating material to reduce friction and/or increase strength. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

It should be recognized that barrel 14 and plunger 16 can have any cross-sectional shape, such as circular and non-circular, including oval or polygonal shapes. In the embodiments where barrel 14 and plunger 16 have a circular cross sectional shaped the outer dimensions of these components are the outer diameters thereof. Furthermore, it is contemplated by the present invention for the cross-sectional shape to vary along the length of barrel 14 and/or plunger 16. For example, barrel 14 can have a circular insertion tip 20, an ovoid main section 22, and a polygonal finger grip 24.

It should also be noted that the terms "first", "second", and "third" and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the disclosure without departing from the scope thereof. Therefore, it is intended that the present invention not be limited to the particular embodiment(s) disclosed as the best mode contemplated for carrying out this invention, but that the invention will include all embodiments falling within the scope of the appended claims.

What is claimed is:

1. A tampon applicator assembly comprising:
a barrel having a first end and a second end opposite said first end, said barrel having a tubular shape and a longitudinal axis that is substantially straight, said barrel having an insertion tip at said first end, a fingergrip proximal to said second end, and a tapered main section adjacent said insertion tip and said finger grip,
said tapered main section having a maximum outer diameter located directly adjacent to said finger grip and a first wall taper that decreases in diameter from said finger grip to said insertion tip, said first wall taper having a taper ratio of about 1.07 to about 1.15,
said insertion tip having a second wall taper that decreases from said tapered main section to a distal end of the insertion tip,
said finger grip having a shoulder region adjacent to said tapered main section, a gripping region adjacent to said shoulder region, and a flared region adjacent to said gripping region opposite said shoulder region, wherein said shoulder region decreases in diameter from said tapered main section to said gripping region, and wherein said flared region has an outer diameter that continuously increases from said gripping region to said second end of said barrel, and wherein said shoulder region and said flared region can mitigate slipping of a user's fingers from said gripping region;
a plunger being slidably received in said barrel; and
a pledget being disposed in said barrel so that a force applied on said plunger expels said pledget from said barrel at said insertion end,
wherein said maximum outer diameter is located from said insertion tip about 55% to 85% of an overall length of said barrel.

2. The assembly as in claim 1, wherein said maximum outer diameter is located from said insertion tip about 60% to 75% of said overall length of said barrel.

3. The assembly as in claim 1, wherein said first wall taper has said taper ratio that is about 1.08 to about 1.13.

4. The assembly as in claim 1, wherein said insertion tip further comprises a plurality of petals.

5. The assembly as in claim 1, wherein said second wall taper has a taper ratio of between about 0.66 and about 1.6.

6. The assembly as in claim 1, wherein said second wall taper has a taper ratio is between about 0.7 and about 0.9.

7. The assembly as in claim 4, wherein said plurality of petals have a petal length-to-width ratio of about 0.8 to about 3.

8. The assembly as in claim 7, wherein said petal length-to-width ratio is over about 2.

9. The assembly as in claim 1, wherein said shoulder and flared regions each have an outer diameter that is about 10% to about 30% larger than an outer diameter of said gripping region.

10. The assembly of claim 1, wherein said insertion tip has a plurality of petals and said second wall taper has a taper ratio of more than about 0.66.

11. The assembly of claim 1, wherein said insertion tip has a plurality of petals, and wherein said plurality of petals have a petal length-to-width ratio over about 2 to about 3.

12. The assembly as in claim 1, wherein said tapered main section is tapered linearly from said maximum outer diameter to said insertion tip.

13. The assembly as in claim 1, wherein said plunger has a plunger main body between a plunger first end and a plunger second end, and wherein said plunger first end has a first outer diameter that is larger than a main outer diameter of said plunger main body.

14. The assembly as in claim 13, wherein said plunger second end has a gradual enlargement or taper from said plunger main body that is greater than said main outer diameter.

15. The assembly as in claim 1, wherein said plunger has a plunger main body portion between a plunger first end and a plunger second end, and wherein said plunger main body portion has a plunger main body diameter that is less than said diameter of said gripping region so that said plunger main body portion is movable through said gripping region to expel said pledget from said barrel.

16. The assembly as in claim 1, wherein said flared region has an outer diameter that is about 15% larger than said diameter of said gripping region.

17. The assembly as in claim 1, wherein said flared region has an outer diameter that is about 25% larger than said diameter of said gripping region.

\* \* \* \* \*